United States Patent [19]
Zdarsky

[11] Patent Number: 5,827,060
[45] Date of Patent: Oct. 27, 1998

[54] DISPENSER FOR MARKER DISKS

[75] Inventor: Constantin Zdarsky, Palm Beach, Fla.

[73] Assignee: Vereinigte Dentalwerke Antaeos Beutelrock Zipperer Zdarsky Ehrler GmbH & Co. KG, Germany

[21] Appl. No.: 675,908

[22] Filed: Jul. 5, 1996

[30] Foreign Application Priority Data

May 31, 1996 [DE] Germany .................. 196 22 033.5

[51] Int. Cl.⁶ .................................................. A61G 15/00
[52] U.S. Cl. ........................ 433/77; 433/72; 206/369; 206/445
[58] Field of Search ......................... 433/72, 75, 77, 433/81, 102, 224; 206/368, 369, 445; 221/246, 288

[56] References Cited

U.S. PATENT DOCUMENTS

| | | | |
|---|---|---|---|
| 1,904,386 | 4/1933 | Raymond | 206/445 |
| 2,251,405 | 8/1941 | Holland | 221/288 |
| 2,506,311 | 3/1950 | Clarke | 221/246 |
| 2,877,927 | 3/1959 | King, Jr. | 221/246 |
| 3,295,208 | 1/1967 | Redtenbacher | 433/72 |
| 3,911,587 | 10/1975 | Forrest et al. | 433/72 |
| 4,182,040 | 1/1980 | Bechtold, Jr. | 433/77 |
| 4,557,690 | 12/1985 | Randin | 433/102 |
| 5,154,611 | 10/1992 | Chen | 433/72 |

FOREIGN PATENT DOCUMENTS 3419712  3/1993  Germany .

*Primary Examiner*—Ralph A. Lewis
*Attorney, Agent, or Firm*—Foley & Lardner

[57] ABSTRACT

The invention relates to a dispenser for marker disks which limit the depth of penetration of root-canal preparatory instruments or the like. The dispenser is composed of a box assembly composed of base 1 and cover 2. The space between the base 1 and cover 2 at least in part evinces a height approximately equal to the thickness of the marker disks. A guide 8 is provided to select the marker disks and to place a marker disk at a specified site. In the zone of this site are present a puncture aperture 7 in the base 1 and an opening 6 in the cover 2. The opening 6 in the cover 2 is at least large enough to pass a marker disk 4. The box assembly composed of base 1 and cover 2 is arranged in an insertion case 5 of such design that for the inserted state of the box assembly, said insertion case will close the aperture 6 in the cover 2.

12 Claims, 2 Drawing Sheets

DISPENSER FOR MARKER DISKS

FIELD OF THE INVENTION

The invention relates to a dispenser for marker disks. Marker disks are useful to limit the depth of penetration of, for example, dental root-canal preparatory instruments. A dispenser according to this invention is composed of a base and a spaced-apart cover, wherein the space between the base and cover is at least at some location approximately equal to the thickness of the marker disks. This dispenser is further provided with a guide to select the marker disks and to place a marker disk at a specified site, said site including a puncture-aperture in the cover large enough to allow passage for a marker disk.

BACKGROUND OF THE INVENTION

Root-canal preparatory instruments may penetrate the root canal only to a specified depth and therefore marker disks made, for instances, of silicone or rubber are used as stops to indicate this depth on the root-canal preparatory instrument. Accordingly, prior to the use of the root-canal preparatory instrument, a marker disk is slipped onto the said instrument and moved to a location along the instrument which is the desired limit of the penetration of said instrument into the root canal.

Marker-disk dispensers are, in general, useful to facilitate the affixation of the marker disks to the root-canal preparatory instrument by assuring that a marker disk is placed at a given site such that it may be impaled by the root-canal preparatory instrument. It is further necessary that, while indicating the depth of penetration on said instrument, the root-canal preparatory instrument together with the impaled marker disk can be removed from the dispenser.

A dispenser of this kind is known from German patent 34 19 712 C2. The marker-disk dispenser disclosed in that patent achieves selective placement of the marker disk such that the disk may be impaled and removed by a feed mechanism. The feed mechanism closes the aperture in the cover in the inactive state to prevent marker disks from falling out. In the active state, the mechanism opens the cover aperture while simultaneously ensuring that a marker disk is present under the cover aperture. Such a feed mechanism represents an additional component of a fairly complex shape making the dispenser design more difficult.

SUMMARY OF THE INVENTION

The object of the invention is to design a dispenser which reliably provides a marker disk for easy engagement by a root canal preparatory instrument in a simple manner so as to allow economic manufacture. The invention achieves this objective by providing an insertion-case that receives a box-assembly such that the case will mask the cover aperture when the box assembly is inserted into the insertion-case.

According to this design, instead of a feed mechanism, a simple insertion-case performs the function of sealing the discharge aperture in the cover when the box construction of the dispenser is inserted into the case in the inactive state. In order to remove a marker disk from the dispenser, the insertion-case is pushed back far enough to reveal the cover aperture. The removal of the marker disk below is then carried out by passing a root-canal preparatory instrument through the cover aperture and impaling the marker disks in the process the instrument passes through the puncture aperture in the base.

Further advantages of the dispenser according to the invention include that this dispenser is free of complex, mechanical selection components and is easily refillable because the base and the cover of this box assembly are easily separated (e.g., by pulling off an adhesive strip holding them together).

The box-assembly and the insert may be made of the same material, as a result of which the dispenser after use in the form of segregated waste or it can be recycled in segregated manner. The manufacture of the dispenser of the invention is very economical.

Additional features of the invention are the subject of the subordinate claims and will be further explained along with additional advantages of the invention with the aid of an embodiment.

DESCRIPTION OF THE DRAWINGS

An exemplary embodiment of the invention is illustrated in the drawings, in which.

DESCRIPTION OF THE PREFERRED EMBODIMENTS

Figure 1:
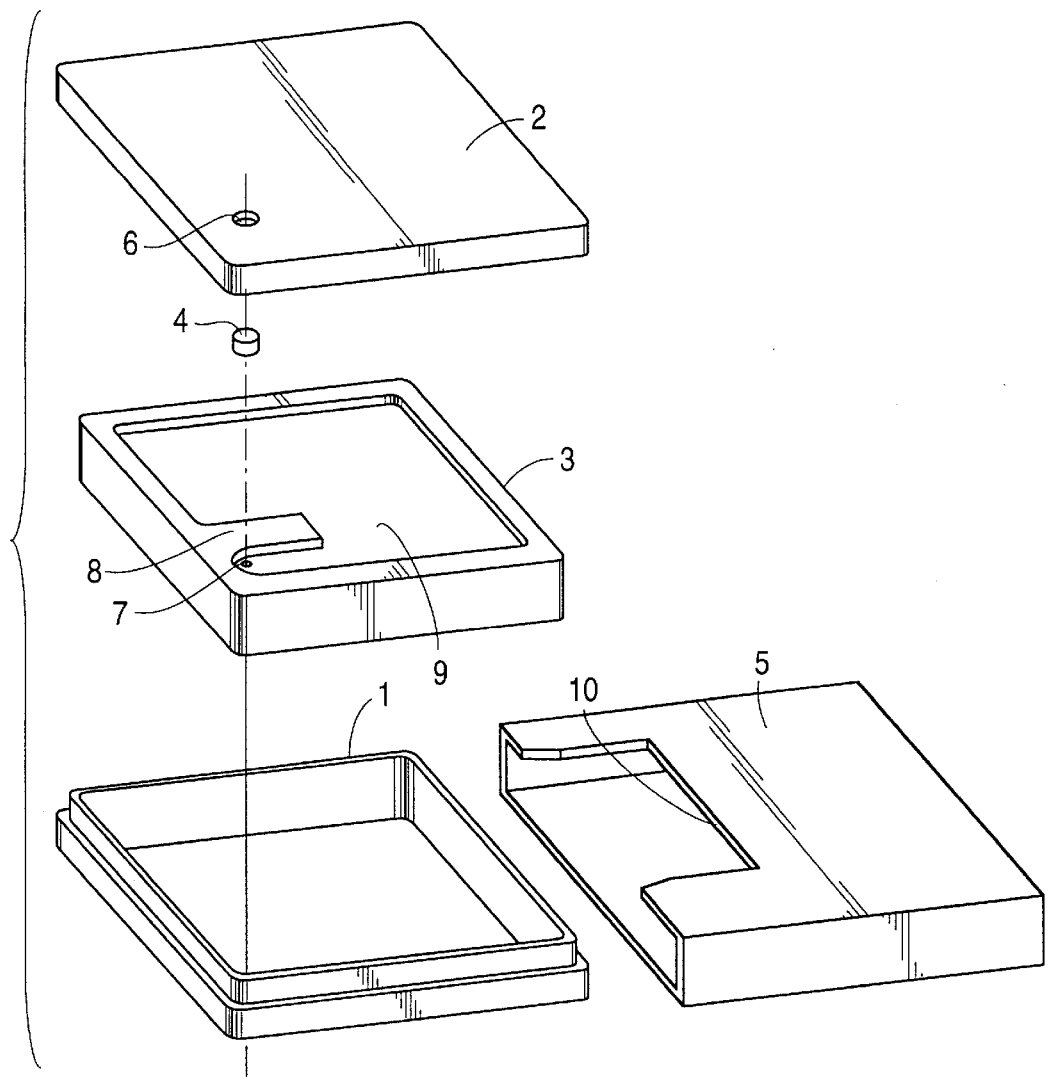
FIG. 1 is an exploded perspective of the components of the embodiments.
Figure 2:
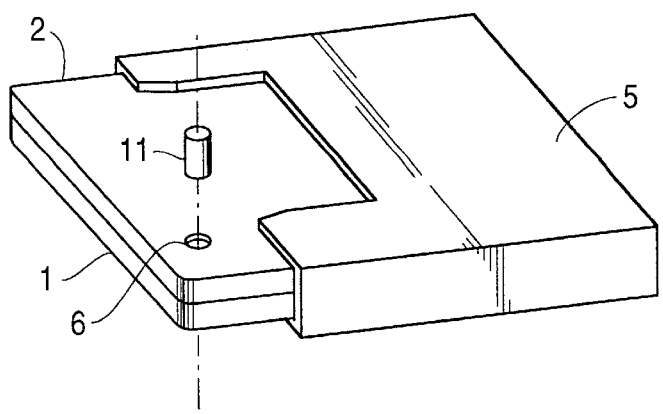
FIG. 2 is a perspective of the embodiment when assembled and during removal of a marker disk.

The dispenser for marker disks 4 is shown in FIGS. 1 and 2. Marker disks are used to limit the depth of penetration of root-canal preparatory instruments. As shown in FIG. 2, the dispenser essentially comprises a base 1, a cover 2, an insert 3 mounted to the base 1 and an insertion-case 5 into which the box assembly composed of base 1, cover 2 and insert 3 is introduced.

Figure 3:
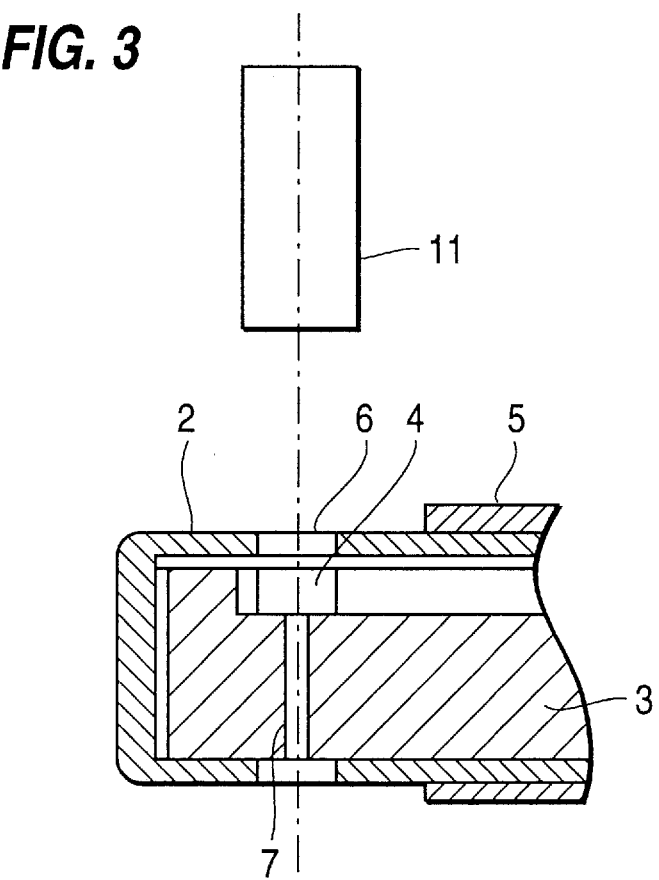
FIG. 3 is a partial cross-section of the removal zone of the embodiment and illustrates how a marker disk is removed by a dental root-canal preparatory instrument.

The insert 3 is designed so that it is provided with a recess on the upper side of the insert 3, the recess having a depth defined by the bottom surface of the recess and the cover 2 when the box assembly is assembled. The depth of the recess substantially corresponds to the thickness of a marker disk 4 at least at one site 9. FIG. 1 illustrates a guide for marker disks 4 provided in the form of a tab 8. Tab 8 runs parallel to the edge of insert 3 at a spacing substantially corresponding to the width of a marker disk 4. The guide assures that the marker disks 4 can be selected individually and that one marker disk 4 is reliably present at a specified location in the insert 3. In FIG. 3, this location is shown as the closed end of the gap bounded by the tab 8 and the edge of the insert 3.

A puncture aperture 7 is present in the insert 3 at the closed end of the gap where a marker disk 4 is reliably located. Puncture aperture 7 is large enough to pass a root-canal preparatory instrument. A corresponding aperture is located in the base 1. At that site the cover 2 is provided with an aperture 6 sized such that marker disk 4 can pass through.

The insert 3 may be made of a deep-drawn plastic foil or of a milled-out plastic.

The box assembly, composed of base 1, cover 2 and insert 3, can be removably placed within the insertion-case 5 (hereinafter "the inserted state"). The insertion-case 5 is designed so that, when in the inserted state, the insertion case seals the aperture 6 in the cover 2 to prevent marker disks from falling out. In the embodiment shown in FIG. 1, the insertion-case 5 includes a right-angle cut-out 10 located in the top wall of the insertion-case 5, positioned asymmetrically (relative to the longitudinal axis of the insertion-case 5), such that said cut-out is bounded by edges of different widths. In the inserted state the larger width edge of the insertion-case will seal the aperture 6 in the cover 2.

A marker disk 4 can be removed from a dispenser of the above design in a manner detailed in FIGS. 2 and 3. In order to remove a marker disk, the box-assembly in the inserted state is moved out of the insertion-case 5 (or the insertion-case 5 is moved back) at least to such an extent that the aperture 6 in the cover 2 is uncovered. Because of the design of the bottom surface of the recess in insert 3 and of tab 8, only one marker disk 4 will reliably be underneath this aperture 6 at a time. Therefore, when a root-canal preparatory instrument 11 passes through the aperture, the instrument will impale the marker disk 4 below the aperture 6, will pass through the puncture aperture 7 in the insert 3 and will pass through the aperture in the base 1 below. This penetration continues until the marker disk 4 has been pushed up to the position corresponding to the permissible depth of penetration in the root canal. The root-canal preparatory instrument 11 is thereupon removed together with the raised marker disk 4 through the aperture 6 in the cover 2 and is thereupon ready for use.

The base 1, the cover 2 the insert 3 and the insertion case 5 may be made of plastic, from a plastic foil for instance. Accordingly, a dispenser allowing reliable removal of individual marker disks 4 and reliable sealing of the dispenser when not in operation is provided with a simple design capable of economic manufacture.

I claim:

1. A dispenser for marker disks comprising:

a base including a recess for storing a plurality of marker disks, the recess having a bottom surface;

a cover for covering the recess and releasably engaging the base;

a puncture aperture disposed in the bottom surface of the recess;

an access aperture in the cover for providing access to the recess, the access aperture being sized to allow through-movement of the marker disks, the access aperture disposed such that when the cover releasably engages the base, the access aperture is adjacent the puncture aperture;

a guide for guiding one marker disk adjacent the access aperture;

an insertion case having a first wall, the insertion case configured to receive the base and cover such that the first wall covers the access aperture.

2. The dispenser of claim 1 wherein each of the marker disks has a thickness and the recess has a depth defined by the bottom surface of the recess and the cover when the cover is engaging the base and wherein the depth of the recess is approximately the thickness of the marker disk.

3. The dispenser of claim 1 wherein a cut-out is provided in the first wall.

4. The dispenser of claim 3 wherein the first wall has first and second remaining portions adjacent the cut-out, the cut-out being configured such that the first remaining portion of the first wall is larger than the second remaining portion of the first wall.

5. A dispenser for marker disks comprising:

a base configured to receive an insert;

an insert including a recess for storing a plurality of marker disks, the recess having a bottom surface, wherein the insert is releasably mounted in the base;

a cover for covering the recess of the insert, the cover configured to releasably engage the base;

a puncture aperture disposed in the bottom surface of the recess;

an access aperture in the cover for providing access to the recess, the access aperture being sized to allow through-movement of the marker disks, the access aperture disposed such that when the cover releasably engages the base, the access aperture is adjacent the puncture aperture;

a guide for guiding one marker disk adjacent the access aperture;

an insertion case having a first wall, the insertion case for receiving the base, insert and cover such that the first wall covers the access aperture.

6. The dispenser of claim 5 wherein the bottom surface of the recess is configured such that the depth of the recess is not equal over the entire bottom surface.

7. The dispenser of claim 5 wherein each of the marker disks has a thickness and the recess has a depth defined by the bottom surface of the recess and the cover when the cover is engaging the base and wherein the depth of the recess is approximately the thickness of the marker disk.

8. The dispenser of claim 5 wherein a cut-out is provided in the first wall.

9. The dispenser of claim 8 wherein the first wall has first and second remaining portions adjacent the cut-out, the cut-out being configured such that the first remaining portion of the first wall is larger than the second remaining portion of the first wall.

10. The dispenser of claim 5 wherein the marker disk has a diameter, wherein the insert has a first edge, and wherein the guide comprises a tab protecting from the bottom surface of the insert, the tab being disposed parallel to the first edge at a distance approximately equal to the marker disk diameter.

11. The dispenser of claim 5 wherein the insert is composed of a deep-drawn plastic foil.

12. The dispenser of claim 5 wherein the insert is a milled-out plastic part.

* * * * *